US011788998B1

(12) United States Patent
Shaalan

(10) Patent No.: US 11,788,998 B1
(45) Date of Patent: Oct. 17, 2023

(54) ETHYLENE SENSOR AND METHOD OF MAKING SAME

(71) Applicant: KING FAISAL UNIVERSITY, Al-Ahsa (SA)

(72) Inventor: Nagih Mohammed Shaalan, Al-Ahsa (SA)

(73) Assignee: KING FAISAL UNIVERSITY, Al-Ahsa (SA)

(*) Notice: Subject to any disclaimer, the term of this patent is extended or adjusted under 35 U.S.C. 154(b) by 0 days.

(21) Appl. No.: 18/157,804

(22) Filed: Jan. 20, 2023

(51) Int. Cl.
G01N 33/00 (2006.01)
G01N 27/04 (2006.01)
G01N 27/30 (2006.01)
G01R 1/067 (2006.01)
G01N 3/00 (2006.01)
C23C 14/22 (2006.01)
(Continued)

(52) U.S. Cl.
CPC ....... *G01N 33/0047* (2013.01); *B23K 26/362* (2013.01); *C23C 14/228* (2013.01); *C23C 14/5873* (2013.01); *G01N 3/00* (2013.01); *G01N 27/045* (2013.01); *G01N 27/30* (2013.01); *G01N 33/0011* (2013.01); *G01R 1/06755* (2013.01); *B23K 2101/36* (2018.08); *G01N 2027/222* (2013.01)

(58) Field of Classification Search
CPC .. G01N 33/0047; G01N 33/0011; G01N 3/00; G01N 27/047; G01N 27/30; B23K 26/362; C23C 14/228; C23C 14/5873; G01R 1/06755
See application file for complete search history.

(56) References Cited

U.S. PATENT DOCUMENTS 11,070,895 B2 7/2021 Taylor
11,078,020 B2 8/2021 Bohling
(Continued)

FOREIGN PATENT DOCUMENTS

EP 3685656 A1 7/2020
JP 2019092419 A 6/2019

OTHER PUBLICATIONS

Esser, Birgit, et al. "Selective detection of ethylene gas using carbon nanotube-based devices; utility in determination of fruit ripeness." Angewandte Chemie International Edition 51.23 (2012): 5752-5756.

*Primary Examiner* — Robert J Eom
(74) *Attorney, Agent, or Firm* — Nath, Goldberg & Meyer; Richard C. Litman

(57) ABSTRACT

The ethylene sensor is formed from a substrate with a gold thin film layer formed thereon. The substrate may be formed from soda-lime glass with a thickness of approximately 1.0 mm. Correspondingly, the gold layer may have a thickness of approximately 200 nm. The gold layer is divided into first and second regions or electrodes by a variable impedance channel containing $K_{0.003}Au_{0.008}Mg_{0.009}Ca_{0.015}Si_{0.11}Na_{0.175}O_{0.68}$ as an ethylene selective material. The channel may be configured such that first and second sets of interdigitated gold fingers are defined in the first and second regions or electrodes, respectively. An ohmmeter is connected to the first and second regions to measure a resistance therebetween. A reference resistance is initially measured that is indicative of an absence of ethylene. Subsequent measurements of the resistance are compared against this reference resistance, with variations in the measured resistance indicating the presence of ethylene.

9 Claims, 5 Drawing Sheets

(51) Int. Cl.
*C23C 14/58* (2006.01)
*B23K 26/362* (2014.01)
*B23K 101/36* (2006.01)
*G01N 27/22* (2006.01)

(56) References Cited

U.S. PATENT DOCUMENTS

| | | |
|---|---|---|
| 2010/0198521 A1 | 8/2010 | Haick |
| 2014/0291170 A1 | 10/2014 | Goecks et al. |
| 2020/0111342 A1 | 4/2020 | Hummer et al. |
| 2020/0166494 A1 | 5/2020 | Ensor et al. |
| 2021/0190747 A1 | 6/2021 | Cobley et al. |
| 2021/0396730 A1 | 12/2021 | Zhang et al. |
| 2022/0252564 A1 | 8/2022 | Hou-Broutin et al. |
| 2022/0276197 A1 | 9/2022 | Buchanan et al. |

ETHYLENE SENSOR AND METHOD OF MAKING SAME

BACKGROUND

1. Field

The disclosure of the present patent application relates to the detection of gases, and particularly to an ethylene sensor and method of making same for detecting the presence of ethylene.

2. Description of the Related Art

Ethylene, the smallest plant hormone, plays a role in many developmental processes in plants. For example, ethylene initiates the ripening of fruit, promotes seed germination and flowering, and is responsible for the senescence of leaves and flowers. The rate-limiting step in the biosynthetic pathway to ethylene is catalyzed by 1-aminocyclopropane-1-carboxylic acid (ACC) synthase. Ethylene production in plants is induced during several developmental stages, as well as by external factors. The ripening process is the result of ethylene binding to the receptor ETR1, which leads to the translation of ripening genes and eventually the production of enzymes that induce the visible effects of ripening. The monitoring of the ethylene concentration is of utmost importance in the horticultural industries.

The internal ethylene concentration in fruit can serve as an indicator for determining the time of harvest, while the monitoring of the atmospheric ethylene level in storage facilities and during transportation is crucial for avoiding over ripening of fruit. At present, detectors for ethylene used in horticulture and in food services are typically either micro-gas chromatography sensors, optical sensors, or surface acoustic wave (SAW) sensors. Although sufficient for detecting and measuring ethylene levels, such sensors are highly specialized equipment, and as such, are very expensive to produce. Further, each of these types of sensors functions via multiple operational steps, thus necessitating a number of different parts and sub-systems, which increases the rate of equipment repair and replacement. Thus, an ethylene sensor and a method of making same solving the aforementioned problems is desired.

SUMMARY

The ethylene sensor is formed from a substrate having a gold thin film layer formed thereon. For example, the substrate may be formed from soda-lime glass. The gold layer is divided into first and second regions or electrodes by a channel containing $K_{0.003}Au_{0.008}Mg_{0.009}Ca_{0.015}Si_{0.11}Na_{0.175}O_{0.68}$ as an ethylene selective material. The channel may be shaped such that first and second sets of interdigitated gold fingers are defined in the first and second regions or electrodes, respectively. An ohmmeter is connected to the first and second regions or electrodes to measure the resistance between the regions or electrodes. A reference resistance is initially measured that is indicative of an absence of ethylene gas in the presence of the sensor. Subsequent measurements of the resistance are compared against this reference resistance. Variations in the measured resistance indicate the presence of ethylene gas.

To make the ethylene sensor, the gold layer is first deposited on the substrate. It should be understood that the gold may be deposited on the substrate using any suitable deposition method, such as thin film physical vapor deposition (PVD), for example. An example of PVD is direct current (DC) sputtering deposition. Following formation of the gold thin film layer, the channel is etched into the gold layer using a carbon dioxide laser. The carbon dioxide laser produces a laser beam in the infrared range. For example, the beam may have a wavelength of 10.6 μm. The etching of the gold layer on the soda-lime glass produces the $K_{0.003}Au_{0.008}Mg_{0.009}Ca_{0.015}Si_{0.11}Na_{0.175}O_{0.68}$ ethylene selective material. Following etching and formation of the ethylene selective layer, the ohmmeter is connected to the first and second regions to measure the resistance between the regions or electrodes.

These and other features of the present subject matter will become readily apparent upon further review of the following specification and drawings.

BRIEF DESCRIPTION OF THE DRAWINGS

FIG. 2A: an unplated substrate; Fig. B: the substrate plated with a thin gold film; FIG. 2C: etching serpentine interdigitated electrodes with a laser; FIG. 2D: a single completed sensor etched on the substrate.

Similar reference characters denote corresponding features consistently throughout the attached drawings.

DETAILED DESCRIPTION OF THE PREFERRED EMBODIMENTS

Figure 1:
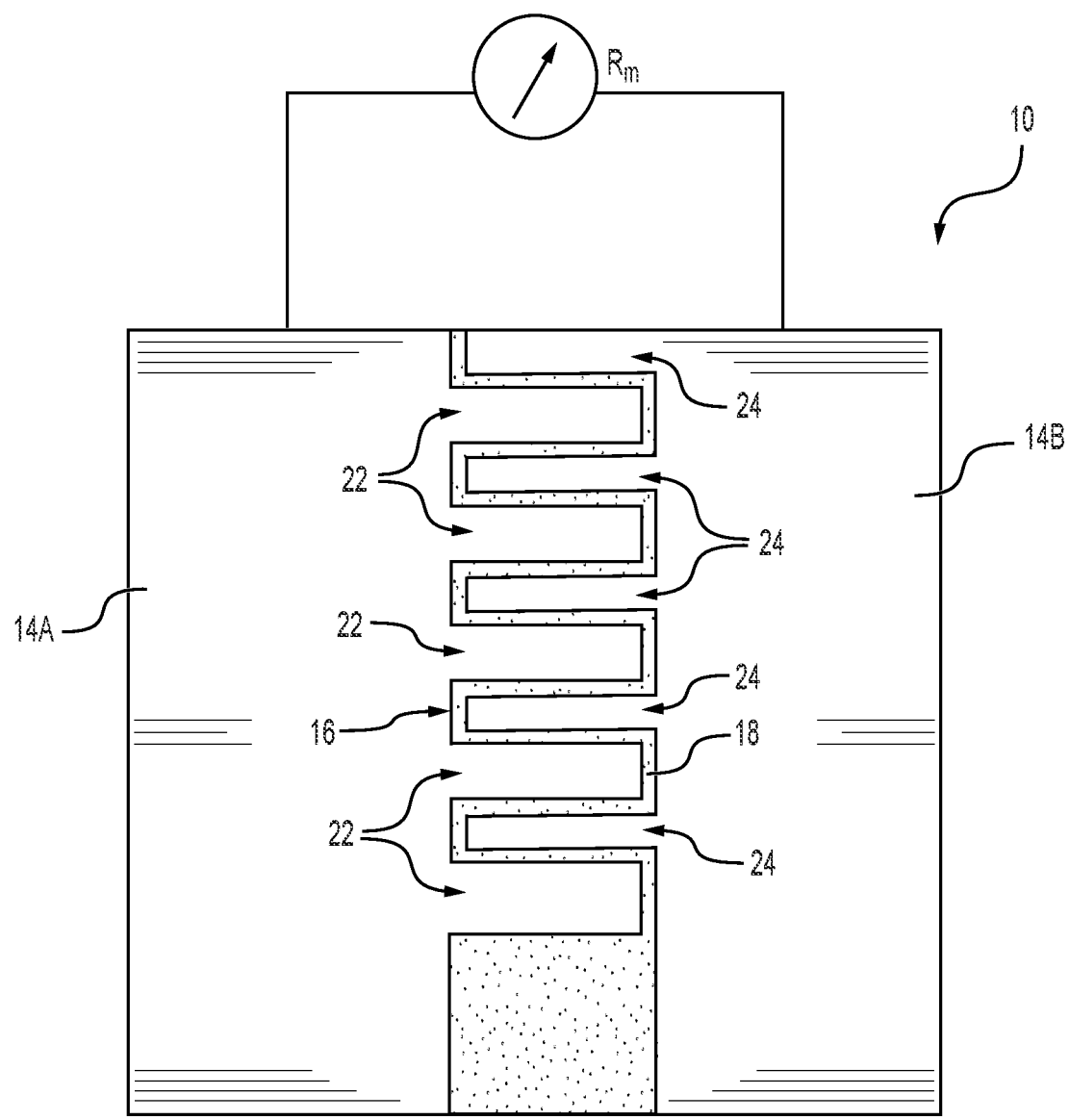
FIG. 1 is a top view of an ethylene sensor.
Figure 2A:
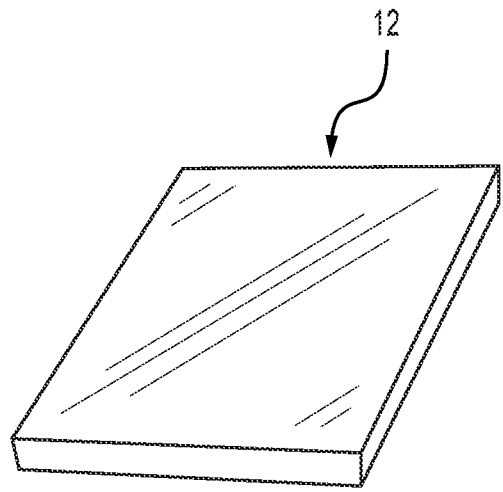
FIGS. 2A, 2B, 2C and 2D are perspective views sequentially illustrate the method of making the ethylene sensor of FIG. 1, including
Figure 2B:
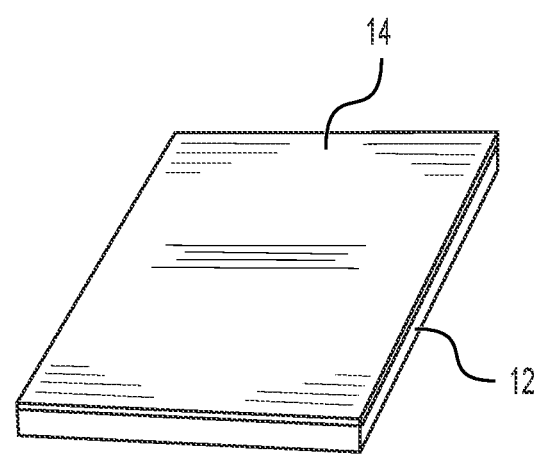
Figure 2C:
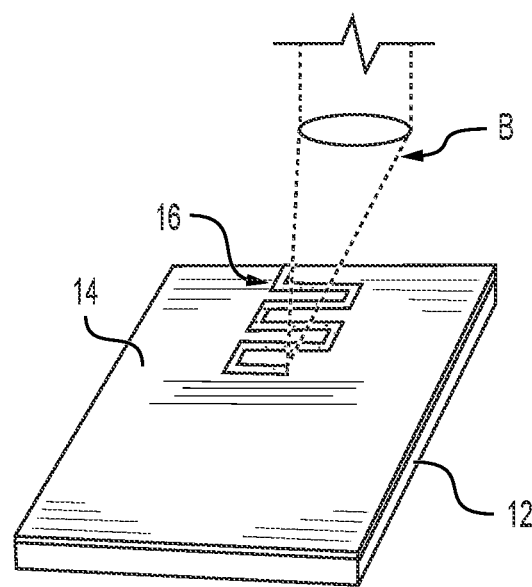
Figure 2D:
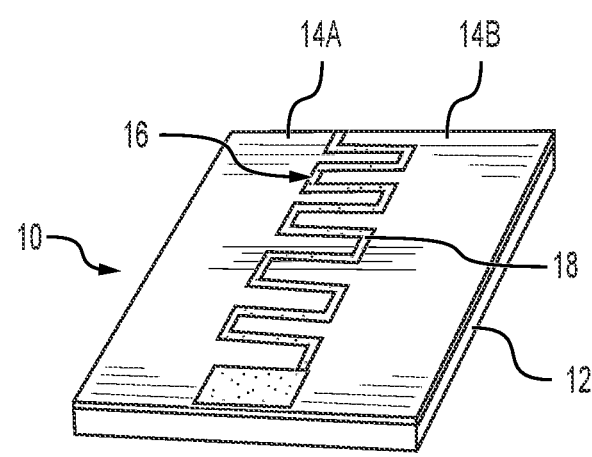

As shown in FIGS. 1 and 2B-2D, the ethylene sensor 10 is formed from a substrate 12 with a gold thin film layer 14 formed thereon. For example, the substrate 12 may be formed from soda-lime glass. As a further example, the substrate 12 may have a thickness of approximately 1.0 mm, and the gold layer 14 may have a thickness of approximately 200 nm. As shown in FIGS. 1 and 2D, the gold layer 14 is divided into first and second regions 14A, 14B or electrodes, respectively, by a channel 16 containing $K_{0.003}Au_{0.008}Mg_{0.009}Ca_{0.015}Si_{0.11}Na_{0.175}O_{0.68}$ as an ethylene selective material 18 having variable impedance.

As shown in FIG. 1, the channel 16 may be shaped such that first and second sets of interdigitated gold fingers 22, 24 are defined in the first and second regions or electrodes 14A, 14B, respectively. It should be understood that the square-wave pattern shown in FIG. 1 is illustrated for exemplary purposes only, and that the channel 16 may have any suitable configuration and relative dimensions. An ohmmeter $R_m$ is connected to the first and second regions r electrodes 14A, 14B to measure a resistance therebetween. A reference resistance is initially measured that is indicative of an absence of ethylene. Subsequent measurements of the resistance are compared against this reference resistance. Variations in the measured resistance indicate the presence of ethylene.

Figure 3:
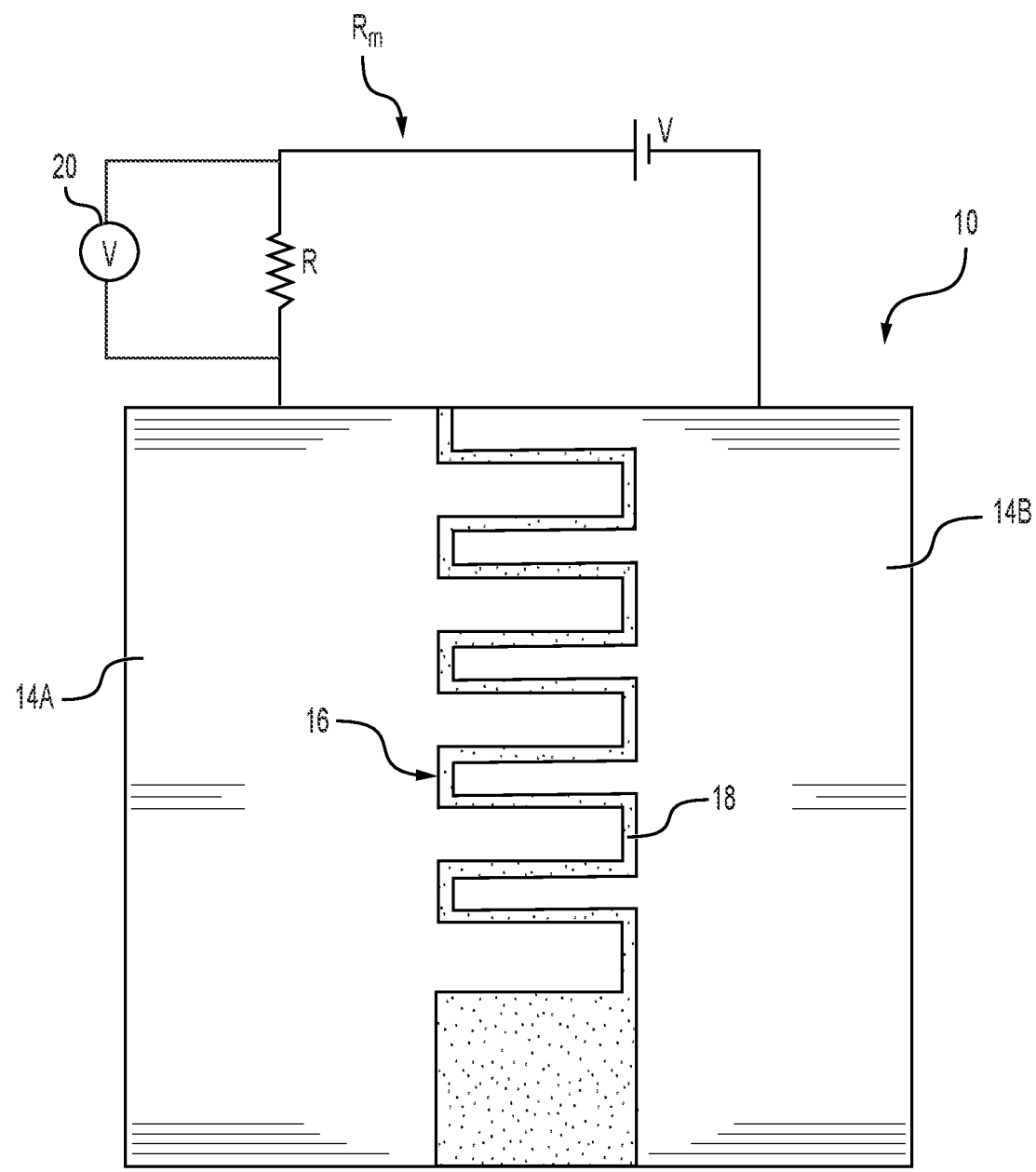
FIG. 3 is a top view of an alternative embodiment of the ethylene sensor.

It should be understood that the ohmmeter $R_m$ may be any suitable type of ohmmeter or resistance sensor. For example, as shown in FIG. 3, ohmmeter $R_m$ may have a conventional ohmmeter circuit formed from a voltmeter 20 for measuring potential across a resistor R having a known resistance, where the resistor R is in series with the sensor 10 (across regions 14A, 14B and channel 16) and a DC voltage source (e.g., a 9 V battery). The voltmeter 20 may be a voltage divider-based voltmeter or the like, as is conventionally known.

Figure 4:
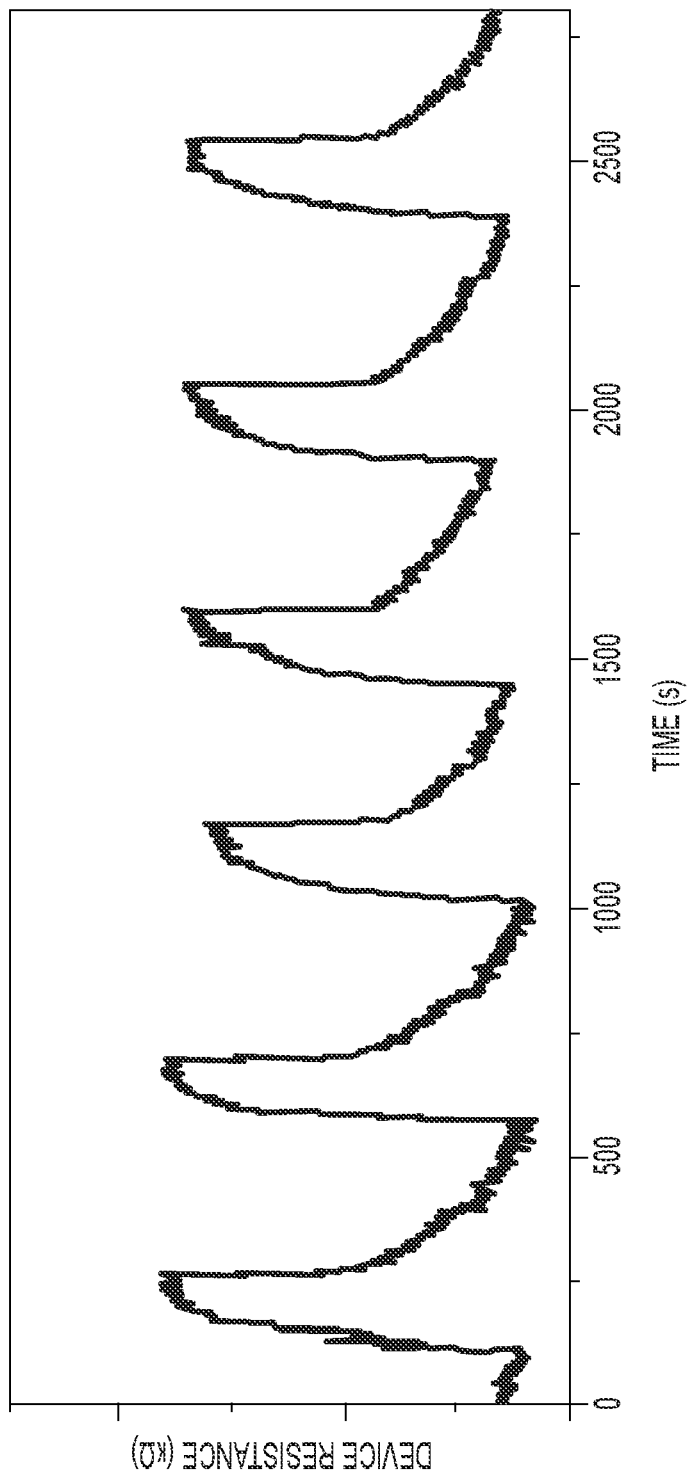
FIG. 4 is a plot of a measured resistance signal as a function of time produced by the ethylene sensor in the presence of ethylene.

In experiments, an ethylene sensor 10 with an ohmmeter $R_m$ constructed as illustrated in FIG. 3 was used to detect the ethylene produced from ripening bananas. The measured resistance signal is displayed in FIG. 4, where the on-off/peak-valley signal pattern is indicative of the presence of ethylene. The signal of FIG. 4 was measured at room temperature with an ethylene concentration of about 0.3 ppm. This data may be used to calibrate the sensor 10, allowing the sensor to be used for both detection and measurement of ethylene concentration based on the measured peak resistance. In the absence of ethylene, the signal will be flat with a constant measured resistance. It is further noted that the resistance has also been found to vary depending on variations in ambient humidity. Thus, the sensor 10 may also be used as a humidity sensor.

As illustrated in FIGS. 2A-2D, in order to make the ethylene sensor 10, the gold layer 14 is first deposited on the substrate 12. It should be understood that the gold layer 14 may be deposited on the substrate 12 using any suitable deposition method, such as thin film physical vapor deposition (PVD). An example of PVD is direct current (DC) sputtering deposition. Following formation of the gold thin film layer 14, the channel 16 is etched into the gold layer 14 using a carbon dioxide laser, as illustrated in FIG. 2C. The carbon dioxide laser produces a laser beam B in the infrared range. For example, the beam B may have a wavelength of 10.6 μm. The etching of the gold layer 14 on the soda-lime glass 12 produces the $K_{0.003}Au_{0.008}Mg_{0.009}Ca_{0.015}Si_{0.11}Na_{0.175}O_{0.68}$ ethylene selective material 18 having an impedance varying with the presence of ethylene vapor in the vicinity of the channel 16.

It should be understood that the carbon dioxide laser may be operated at any suitable output power to produce the $K_{0.003}Au_{0.008}Mg_{0.009}Ca_{0.015}Si_{0.11}Na_{0.175}O_{0.68}$ ethylene selective material 18 in the etched channel 16. For example, the carbon dioxide laser may have a power output between 10.0 W and 11.0 W. Similarly, it should be understood that the beam B produced by the carbon dioxide laser may be moved relative to the gold layer 14 at any suitable speed for etching the channel 16 in the desired configuration for generating the ethylene selective material 18. For example, the beam B may be moved relative to the gold layer 14 at an etching speed between 100 mm/s and 120 mm/s. Following etching and formation of the ethylene selective layer 18, the ohmmeter $R_m$ is connected to the first and second regions or electrodes 14A, 14B to measure the resistance between the regions or electrodes 14A, 14B, as illustrated in FIG. 1.

Figure 5:
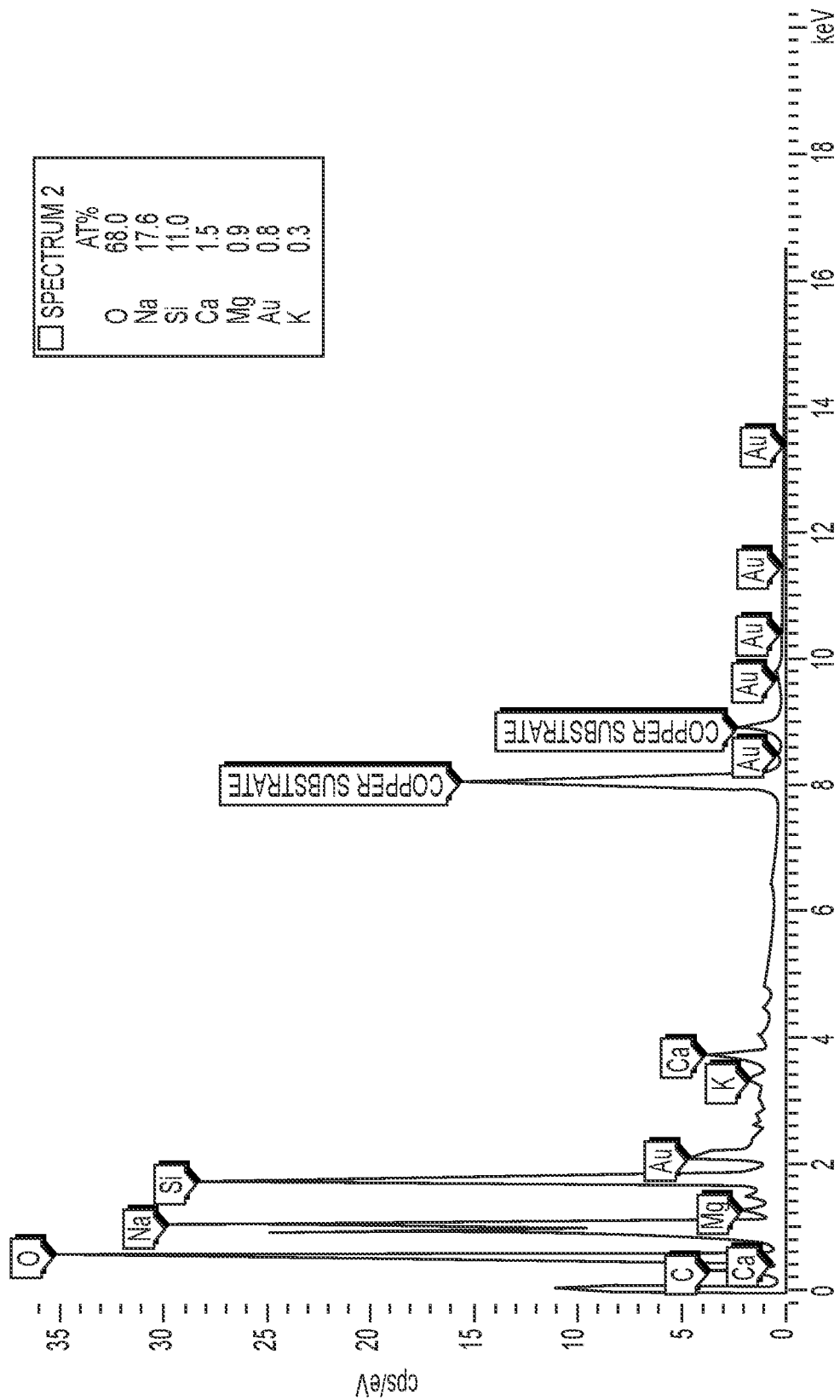
FIG. 5 is an energy dispersive X-ray spectroscopy (EDX) spectrum of results for ethylene selective material formed during laser etching in the method of making the ethylene sensor.

In experiments, a gold target with a purity of 99.999% was attached to the DC-magnetron of a DC sputtering system for DC sputtering on a soda-lime glass slide with a thickness of 1.0 mm. A 200 nm gold thin film layer was formed on the soda-lime glass slide using DC sputtering at 35 W at a pressure of $6 \times 10^{-3}$ mbar in an argon atmosphere. The substrate was held at room temperature. Interdigitated electrodes, such as those shown in FIG. 1, were then formed in the gold layer using a carbon dioxide etching laser under the control of pattern-forming software. Etching was performed using a laser beam with a wavelength of 10.6 μm at a power of between 10.0 W and 11.0 W, and at an etching speed between 100 mm/s and 120 mm/s. Etching was performed in ambient air. The material contained within the etched channel was brown in color and analyzed using energy dispersive X-ray spectroscopy (EDX). The EDX results are shown in FIG. 5 and indicate that the material formed in the channel is $K_{0.003}Au_{0.008}Mg_{0.009}Ca_{0.015}Si_{0.11}Na_{0.175}O_{0.68}$. To exfoliate the synthesized layer from the substrate, the entire sensor was ultrasonicated in deionized water and the suspended layer was deposited on a copper substrate for performing the EDX analysis.

It is to be understood that the ethylene sensor and method of making same is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An ethylene sensor, comprising:
    a substrate;
    a gold layer formed on the substrate, the gold layer being divided into first and second regions by a channel containing an ethylene selective material, the ethylene selective material having an elemental composition of $K_{0.003}Au_{0.008}Mg_{0.009}Ca_{0.015}Si_{0.11}Na_{0.175}O_{0.68}$; and
    an ohmmeter connected to the first and second regions to measure resistance between the regions, a variation in the measured resistance indicating presence of ethylene gas varying impedance of the channel.

2. The ethylene sensor as recited in claim 1, wherein the substrate comprises soda-lime glass.

3. The ethylene sensor as recited in claim 1, wherein the substrate has a thickness of 1.0 mm.

4. The ethylene sensor as recited in claim 3, wherein the gold layer has a thickness of 200 nm.

5. The ethylene sensor as recited in claim 1, wherein the channel defines first and second sets of interdigitated gold fingers in the first and second regions, respectively.

6. A method of making an ethylene sensor, comprising the steps of:
    depositing a 200 nm thick gold layer on a 1.0 mm thick soda-lime glass substrate;
    etching a channel in the gold layer and the soda-lime glass substrate using a carbon dioxide laser to divide the gold layer into first and second electrodes, the channel having varying resistance in the presence of ethylene gas, the etched channel having an elemental composition of $K_{0.003}Au_{0.008}Mg_{0.009}Ca_{0.015}Si_{0.11}Na_{0.175}O_{0.68}$; and
    connecting an ohmmeter to the first and second electrodes to measure resistance between the electrodes;
    wherein the carbon dioxide laser has a power output between 10.0 W and 11.0 W;
    wherein the step of etching the channel comprises moving a beam generated by the carbon dioxide laser at an etching speed between 100 mm/s and 120 mm/s;
    wherein a beam generated by the carbon dioxide laser has a wavelength of 10.6 μm.

7. The method of making an ethylene sensor as recited in claim 6, wherein the step of depositing the gold layer on the substrate comprises depositing the gold layer on the substrate using thin film physical vapor deposition.

8. The method of making an ethylene sensor as recited in claim 7, wherein the step of depositing the gold layer on the substrate comprises depositing the gold layer on the substrate using DC sputtering deposition.

9. The method of making an ethylene sensor as recited in claim 6, wherein the step of etching the channel comprises moving a beam generated by the carbon dioxide laser such that the channel defines first and second sets of interdigitated gold fingers in the first and second electrodes, respectively.

\* \* \* \* \*